United States Patent
Holmes

[19]

[11] Patent Number: 5,827,487
[45] Date of Patent: Oct. 27, 1998

[54] MEDICAL INSTRUMENT FIXATION METHOD AND MEANS

[75] Inventor: Russell P. Holmes, Boston, Mass.

[73] Assignee: Riley Medical, Inc., Auburn, Me.

[21] Appl. No.: 807,812

[22] Filed: Feb. 26, 1997

[51] Int. Cl.[6] .................................................. A61L 2/00
[52] U.S. Cl. ...................... 422/297; 422/297; 422/300; 248/424; 248/172; 248/176.1; 248/298.01; 211/70.6; 206/483; 206/370
[58] Field of Search ............................... 422/300, 297; 248/424, 172, 176.1, 298.1, 346.07; 211/59.1, 70.6; 206/474, 480, 483, 370

[56] References Cited

U.S. PATENT DOCUMENTS

| 337,888 | 3/1886 | Swan . | |
|---|---|---|---|
| 635,284 | 10/1899 | Adair . | |
| 4,135,868 | 1/1979 | Schainholz | 422/310 |
| 4,262,799 | 4/1981 | Perrett | 206/363 |
| 4,317,416 | 3/1982 | Baum et al. | 108/157 |
| 4,573,569 | 3/1986 | Parker | 206/1.7 |
| 4,635,801 | 1/1987 | Oren | 211/70.6 |
| 4,643,303 | 2/1987 | Arp et al. | 206/370 |
| 4,859,423 | 8/1989 | Perlman | 422/102 |
| 5,384,103 | 1/1995 | Miller | 422/310 |
| 5,424,048 | 6/1995 | Riley | 422/300 |
| 5,433,930 | 7/1995 | Taschner | 422/300 |
| 5,441,709 | 8/1995 | Berry, Jr. | 422/297 |
| 5,492,671 | 2/1996 | Krafft | 422/26 |
| 5,525,314 | 6/1996 | Hurson | 422/300 |

OTHER PUBLICATIONS

Sterilization Systems Corporation, The Advanced Laparoscopy/Pelviscopy Sterilization Basket, Protect Your Instruments, 3 pages, no date available.

Primary Examiner—Robert J. Warden
Assistant Examiner—Fariborz Moazzam
Attorney, Agent, or Firm—Cesari and McKenna, LLP

[57] ABSTRACT

A medical instrument fixation system for a sterilization tray having a bottom wall and an array of ventilation holes in the bottom wall, the holes being arranged in columns and rows with a selected spacing between the columns and rows includes a plurality of elongated rails. Each rail has a bottom surface, a top surface and a plurality of projections extending from the bottom surface and spaced apart along each rail a distance equal to, or an intregal multiple of, the selected spacing, the projections being sized to plug into the holes so that the rail extends along a column or row of holes. The system also includes a plurality of posts, each post having opposite ends and means for keying one end of each post to a different one of the rails so that each post can slide along the corresponding rail to a selected position thereon. A method of fixating the instruments in the tray using special retention devices is also disclosed.

7 Claims, 2 Drawing Sheets

MEDICAL INSTRUMENT FIXATION METHOD AND MEANS

This invention relates to the field of sterilization trays. It relates more particularly to improved instrument fixation devices for holding surgical instruments at fixed positions in the tray.

BACKGROUND OF THE INVENTION

Surgical instruments are often transported in trays prior to use. The instruments are usually laid out in a certain way in the tray and subjected to sterilization in a steam autoclave or similar sterilization apparatus. In order to maintain separations between the various instruments in the tray, the instruments are supported or retained by brackets positioned in the tray. Following sterilization, the tray full of instruments may be transported to an operating room and placed close to the surgical team whose members may withdraw the instruments from the tray as needed for a particular surgical procedure. Many times, the instruments are selectively arranged in the tray so that they can be picked from the tray in the general order that they are needed for the particular procedure. Examples of such trays are found in U.S. Pat. Nos. 4,643,303; 5,424,048 and 5,492,671.

As seen from the above patents, the known devices for organizing and fixating medical instruments in a tray include various types of slotted brackets, clips and posts which project up from the bottom of the tray, the instruments being held in place within the slots and clip openings and between the posts. As shown there, a plurality of such fixation devices can be spaced parallel or perpendicular in the tray so that they engage and support the opposite sides or ends of various different length instruments.

Most such fixation devices are able to effectively locate and hold instruments which are more or less straight and regular. However, they are not particularly suitable for fixating oddly shaped and irregular instruments such as retractors and other longer instruments that have ring handles. This is because there is insufficient flexibility in the placement of the various fixation devices within the tray as to enable the devices to closely engage the instruments while still organizing the instruments in an efficient layout within the tray. This results from the fact that the fixation devices are often plugged into the ventilation holes usually present in the bottom of the tray such that a fixation device can only be placed where there are holes in the bottom of the tray.

As the number of such holes is limited by manufacturing cost, required tray bottom strength and the need to prevent the instruments from projecting through the holes, so also are the positions of the various fixation devices. Consequently, either the tray contains too few properly fixated instruments or a larger number of instruments some of which may not be properly fixated. Thus, if the tray is shaken or tilted, those loose instruments may become disengaged from the fixation devices and assume skewed positions in the tray so that they may become damaged and difficult to remove without upsetting other instruments in the tray. In extreme case, these loose instruments may even fall out of the tray and become contaminated. Since a tray may contain a complete set of instruments needed for a particular surgical procedure, this may require that another full tray of sterilized instruments be made available to the surgical team.

Another consideration is that the instruments required to perform a specific surgical procedure may vary greatly between hospitals. Therefore, it is practically impossible to design a standard tray configuration that will be acceptable in more than one hospital. Thus, an optimum instrument fixation arrangement is one which is enormously flexible so that it can be applied to each individual hospital, because the numbers and types of instruments being presented in the trays change constantly. Moreover, the instruments vary greatly in shape and size. Therefore, if these instruments are to be efficiently laid out and fixated within the trays, the fixation devices must be placed at the best holding locations and preferably be spaced no more than ⅛ inch from the instrument's surface. Fixation devices positioned in this manner effectively locate the instruments within the tray, yet allow their quick removal during surgery. Such an arrangement may also facilitate the daily tray assembly by clearly depicting the outlines of the instruments to be presented in the tray.

SUMMARY OF THE INVENTION

Accordingly, the present invention aims to provide a medical instrument fixation device which can be positioned at almost any location in a sterilization tray.

Another object of the invention is to provide such a fixation device which effectively holds the instrument, yet allows its ready removal when needed.

Yet another object of the invention is to provide an instrument fixation device which allows an efficient and effective layout of different instruments in a sterilization tray.

Another object of the invention is to provide a medical instrument fixation system which is particularly suitable for retaining and presenting oddly shaped instruments.

Another object of the invention is to allow the tray configuration to be changed easily without effort at minimal cost.

Other objects will, in part, be obvious and will, in part, appear hereinafter. The invention accordingly comprises the sequence of steps and the apparatus embodying the features of construction, combination of elements and arrangement of parts which will be exemplified in the following detailed description, and the scope of the invention will be indicated in the claims.

Briefly, the fixation device of this invention comprises a rail of optional length and having at least two pegs projecting from its underside which are sized and is spaced apart so as to be able to plug into at least two of the ventilation holes present in the bottom wall of a conventional sterilization tray. These holes are usually arranged in a rectangular array of columns and rows so that the rail can be positioned at any location in that hole array within the resolution of the hole array. The rail may be releasably fixed in position by fastener means secured to the ends of the pegs from the underside of the tray.

The fixation device also includes one or more upstanding posts of optional length which inter-fits with the rail and may be positioned at various locations along the length of the rail. Preferably, means are provided for releasably fixing the post position along the rail.

Resultantly, while the position of each rail within the sterilization tray may be limited to some extent by the spacings of the columns and rows in the hole array at the bottom of the tray, the position of each post relative to the hole array is not so limited. In other words, each post can be positioned at substantially any location on the tray bottom.

The invention thus allows the person who is setting up the tray to lay out the instruments in the tray as specified by the particular hospital or surgeon. Rails of various lengths may then be inserted under the instruments and loosely fastened to the tray. Next, posts may be engaged to the rails and slid down the rails until they are positioned next to the instruments. When the tray is complete and the posts and instruments are positioned correctly, the posts and rails may be tightened down so that the instruments are fixated at their assigned positions within the tray.

Thus, a fixation system incorporating my instrument retention devices is extremely flexible and may be accommodated to many instrument layouts desired within sterilization tray, as well as to irregularly shaped instruments within those layouts. Accordingly, the invention should find wide application in clinics and hospitals which perform surgical procedures and whose routines require a variety of different presentations of the surgical instruments.

BRIEF DESCRIPTION OF THE DRAWINGS

For a fuller understanding of the nature and the objects of the invention, reference should be had to the following detailed description taken in connection with the accompanying drawings, in which.

DESCRIPTION OF THE PREFERRED EMBODIMENTS

A more or less conventional sterilization tray is an integral part of my medical instrument fixation system. The tray has a generally rectangular bottom wall 10a surrounded by upstanding side walls. Formed in the bottom wall 10a is a rectangular array of holes 14 arranged in columns and rows. Typically, the holes are spaced apart about 1½ inch on center. These holes are utilized to set the configuration of the fixation system as will be described.

The fixation system also includes a plurality of instrument retention or fixation devices indicated generally at 16 which are positioned and oriented within the tray and secured to the tray bottom wall 10a, in such a way as to fixate or hold a variety of different medical instruments that have been arranged in a selected layout within the tray.

Figure 3:
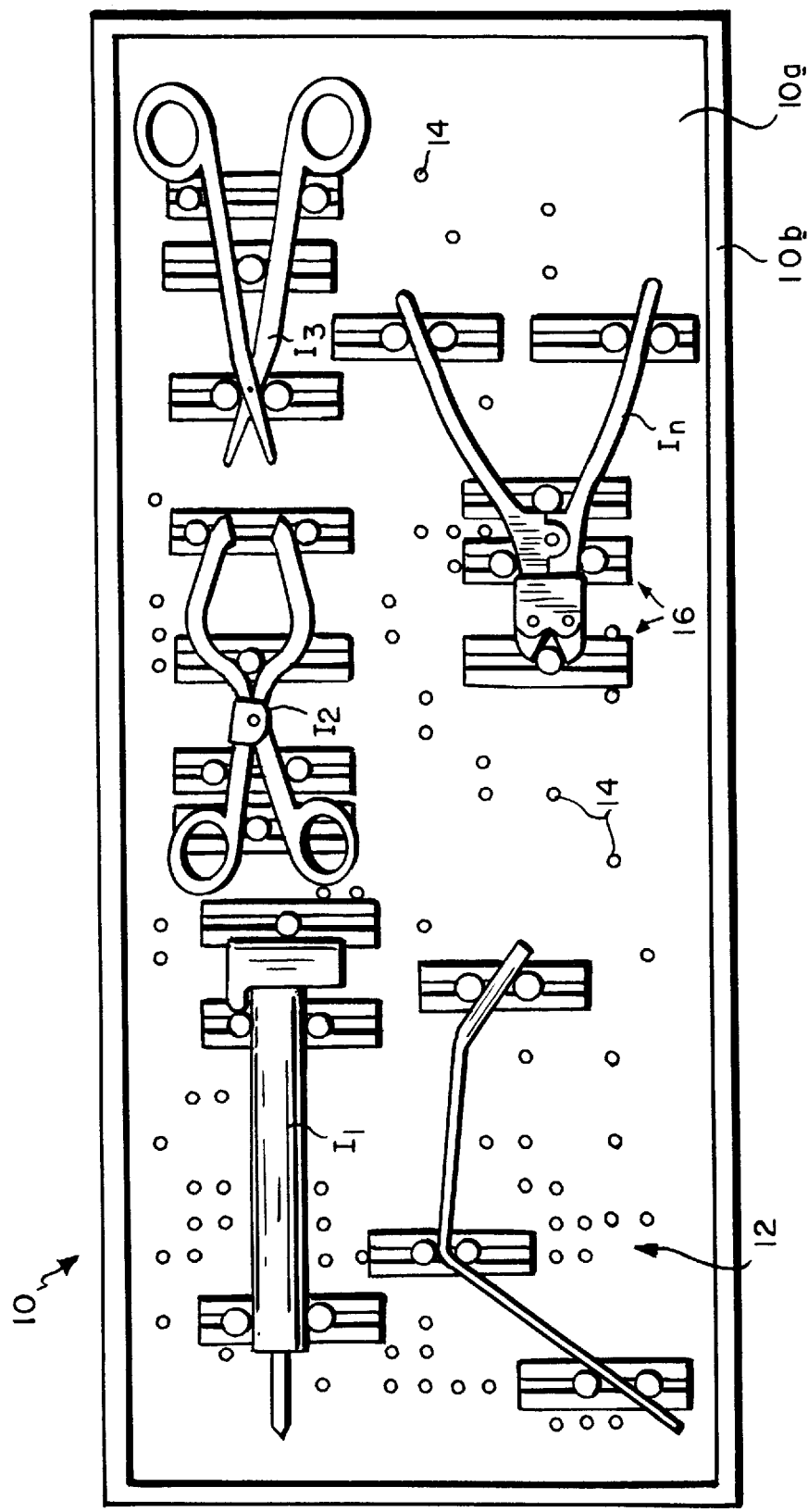
FIG. 3 is a plan view of a tray incorporating an instrumentation fixation system according to the invention.

Refer to FIG. 3 which shows a typical tray 10 having a bottom wall 10a and side wall 10b and with an instrumentation fixation system 12 composed of devices 16 retaining various medical instruments $I_1, I_2, I_3, \ldots I_n$.

Figure 1A:
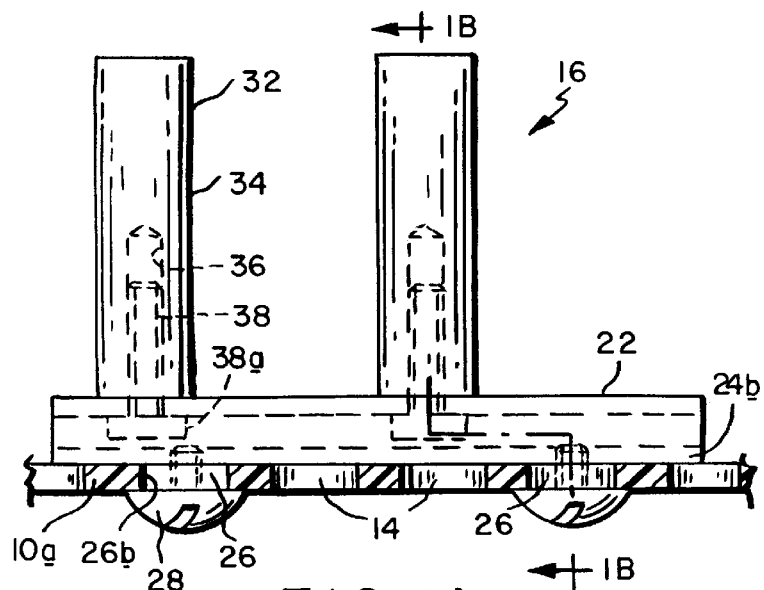
FIG. 1A is a side elevational view on a larger scale illustrating one of the instrument retention devices comprising an instrument fixation system according to the invention.
Figure 1B:
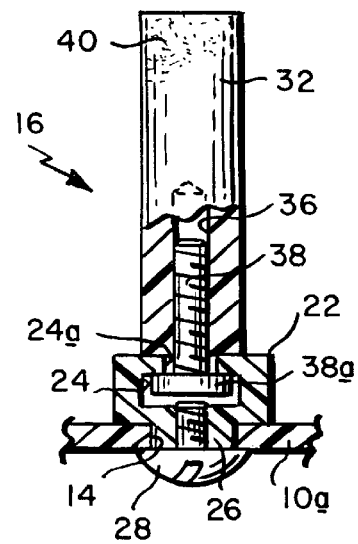
FIG. 1B is a sectional view taken along line 1B—1B of FIG. 1A.

As shown in FIGS. 1A and 1B, each fixation device 16 comprises an elongated generally rectangular rail 22 having a generally C-shaped cross section so that the rail defines a internal keyway 24 which includes an longitudinal slot 24a at the top of the rail. The rails 22 comprising the different fixation devices 16 may come in a variety of lengths, e.g., two, three and five inches.

The bottom wall 24b of each rail 22 is formed with a plurality of depending pegs or collars 26 which are sized to fit in the holes 14 in the tray bottom wall 10a. That is, the outside diameter of each peg 26 is slightly smaller than the diameter of holes 14 and the length of each peg is comparable to the thickness of the tray wall 10a. Furthermore, the centerline distance between adjacent pegs 26 is equal to, or an integral multiple of, the centerline spacing of the holes 14. Thus, the pegs 26 of a three inch long rail 22 depicted in FIG. 1B may be spaced apart a distance such that the pegs can be plugged into holes 14 spaced two holes apart. The rail 22 may be releasably secured to the tray wall 10a by threaded fasteners 28 screwed into the ends of the pegs 26 at the underside of the tray. As shown in FIGS. 1A and 1B, the fasteners 28 are provided with heads which are larger than the tray holes 14 so that the edge margins of the heads engage the underside of tray wall 10a around the perimeters of holes 14.

Still referring to FIGS. 1A and 1B, each fixation device 16 also includes one or more upstanding posts 32 movably mounted to rail 22. The device illustrated in those figures has two such posts 32. Each post 32 includes generally cylindrical sleeve-like nut 34 which may come in a variety of lengths, e.g., 0.5, 1.0 and 1.3 inches. The diameters of the nuts are usually the same, e.g., 0.25 inch. A threaded passage 36 extends in from the lower end of each nut 34 for receiving a threaded fastener 38. Each fastener 38 has a head 38a whose sides are flat as best seen in FIG. 1B so that the head can key into the keyway 24 formed in rail 22 with the shank of the fastener extending out through the slot 24a in the top of the rail. Thus, when the fastener 38 is keyed to the rail as shown in FIGS. 1A and 1B, it cannot rotate relative to the rail; however, it can slide along the keyway 24 in the rail. Each post 32 may be releasably positioned at a selected location along the rail by rotating the nut 34 so that the associated fastener 38 screws into the nut passage 36, thereby gripping the slotted top wall of the rail between the fastener head 38a and the lower end of nut 34.

In order to install the fixation system 12 to fulfill the objectives of the invention, the various instruments should be arranged in the tray at the desired locations for the particular surgical procedure to be performed using those instruments. For example, the instruments may be positioned in the order in which they will be used beginning from one side or end of the tray. Alternatively, the instruments may be arranged so that a maximum number of instruments can be placed in the tray while maintaining adequate spacings of the instruments from each other so that they will not become entangled and so that they can be removed easily when needed.

Once the desired instrument layout has been set, the rails 22 can be inserted under the instruments and loosely attached to the tray bottom wall 10a using fasteners 28 at the positions and orientations to best fixate the overlying instrument particularly at the instrument extremities. Then, the posts 32 may be slid onto the rails 22 from one or both ends such that the post fasteners 38 key into the rail keyways 24. Each post may be moved along the associated rail until it nearly engages the adjacent surface or critical holding area of the associated medical instrument. At that point, the nut 34 of each post may be tightened as needed to fix the position of the post. In this way, a selected instrument layout can be fixed so that even if the tray is tipped or jostled during handling, the instruments will remain in their proper positions within the tray.

It is important to note also that the rails 22 space the instruments above the tray bottom wall 10a assuring good circulation of steam under the instruments during the sterilization process.

Since the arrangement of the fixation devices 16 is customized for each instrument layout, the locations of the posts 32 actually provide a rough outline of the layout. Thus, if particular instruments have to be removed from the tray temporarily, their proper locations in the tray will be obvious from the outlines provided by the associated posts. Actually, the sleeve-like nuts 34 and/or posts 32 that retain the various instruments may be color coded as shown at 40 in FIG. 1B so that the posts for each instrument have a unique color. This also helps to identify the correct position for each instrument in the tray.

Figure 2A:
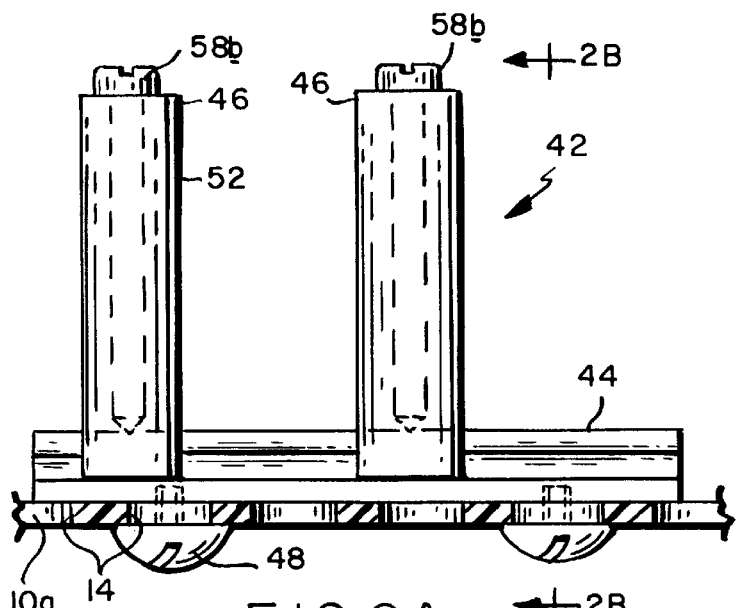
FIG. 2A is a view similar to FIG. 1A showing another retention device embodiment for use in the fixation system.
Figure 2B:
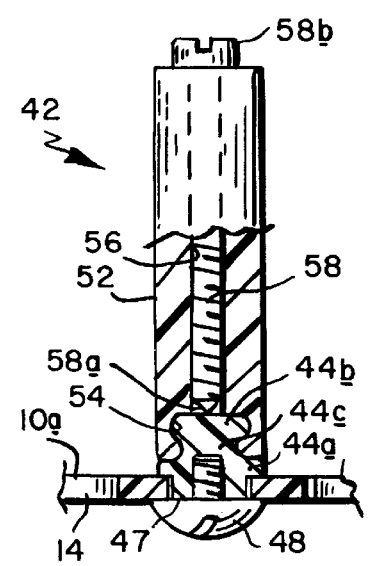
FIG. 2B is a sectional view taken along line 2B—2B of FIG. 2A.
Figure 2C:
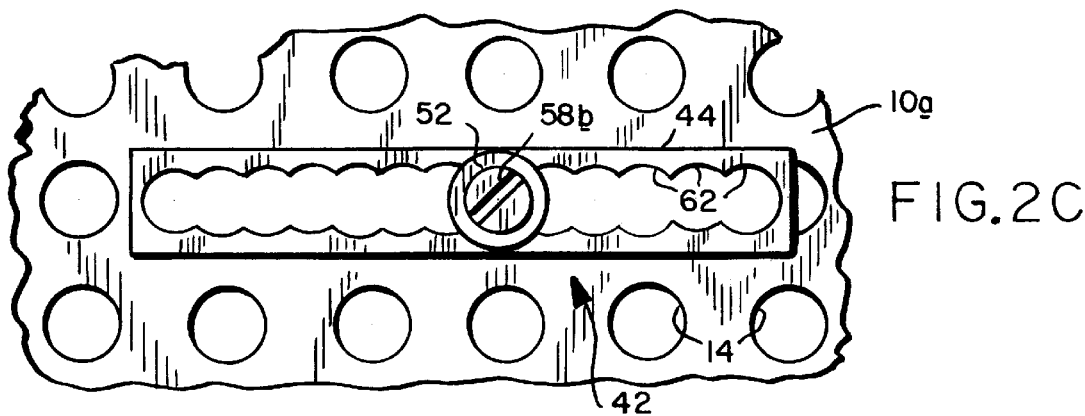
FIG. 2C is a plan view of the FIG. 2A retention device.

Refer now to FIGS. 2A—2C, which show another fixation device 42 for use in the sterilizer tray. The device 42 comprises a rail 44 which supports one or more upstanding posts 46 which may be movably positioned along the rail. In this case, however, the rail 44 is more or less like a railroad track in that it has a relatively wide base 44a and a relatively wide head portion 44b connected by a narrower neck portion 44c as best seen in FIG. 2B. As we shall see, rail 44 functions as a key. A plurality of pegs or collars 47 project from the underside of base 44a which pegs are arranged and adapted to plug into one or another of the holes 14 in the tray bottom wall 10a. The rail 44 may be releasably secured to the tray bottom wall by threaded fasteners 48 in the same manner described above for rail 22.

Each post 46 comprises a tubular sleeve 52 whose lower end is slotted to provide a keyway 54 for the associated rail 44. In other words, the keyway 54 has essentially the same profile as the rail 44 cross section as best seen in FIG. 2B. Also, the sleeve 52 has an axial passage 56 which extends from the top of the sleeve down to keyway 54. Screwed down into passage 56 is a long threaded fastener 58. Fastener 58 is longer than passage 56 so that when the fastener is turned all the way down, its tip 58a will engage the top of the underlying rail 44.

The fastener tip 58a may be pointed as illustrated in FIGS. 2A and 2B. In this event, when the post is slid to the desired position along the rail and the fastener 58 is screwed down, its tip 58a will "bite" into the top of rail 44, thereby fixing the position of the post on the rail.

Alternatively, the tip of the fastener can be made flat and the top of the rail 44 formed with overlapping discoid indentations 62 as illustrated in FIG. 2C. In that event, when the fastener is turned down, its tip will seat in one or another of the indentations 62 thereby fixing the location of the post along the rail. Preferably, the fastener is dimensioned so that the fastener head 58b will seat against the top of sleeve 52 before the fastener tip bottoms in the indentation 62 so that the position of the post on the rail is fixed by the fastener tip engaging the side of the indentation rather than the bottom. This helps to minimize stresses on the post and rail.

It will be appreciated from the foregoing that the fixation system described herein should facilitate the efficient organization of medical instruments in a sterilization tray and effectively hold those instruments in position during the sterilization process and during the transportation of the tray to and from the sterilizing facility. Thus, it assures that the instruments will be protected against damage and presented properly to the medical personnel performing a surgical procedure using those instruments while Is allowing ready removal of the instruments from the tray when needed.

It will be seen that the objects set forth above among those made apparent from the preceding description are efficiently attained. Also, certain changes may be made in the above method and in the constructions set forth without departing from the scope of the invention. For example, the pegs can be designed to snap lit in the holes in the tray bottom wall. Therefore, it is intended that all matter contained in the above description or shown in the accompanying drawings shall be interpreted as illustrative and not in a limiting sense.

It should also be understood that the following claims are intended to cover all of the generic and specific features of the invention described herein.

What is claimed is:

1. A medical instrument fixation system comprising
   a sterilization tray having a bottom wall;
   an array of ventilation holes in the bottom wall said holes being arranged in columns and rows with a selected spacing between the columns and rows;
   a plurality of elongated rails, each rail having a bottom surface and a top surface;
   a plurality of projections extending from the bottom surface and spaced apart along each rail a distance equal to, or an integral multiple of, said selected spacing, the projections being sized to plug into said holes so that each rail extends along a column or row of holes in position for engaging and supporting one or more medical instruments;
   a plurality of posts, each post having
      opposite ends,
      means for keying one end of each post to a different one of said rails so that each post can slide along the corresponding rail to a selected position thereon adjacent to an instrument engaged by the corresponding rail, and
      fixing means for releasably fixing the position of each post on the corresponding rail, said fixing means including a threaded fastener threaded axially through said post, said fastener having an end portion engaging said rail so that when the post and fastener are rotated relatively in one direction, the post is clamped to the rail and when the post and fastener are rotated relatively in the opposite direction the post is unclamped from the rail.

2. The system defined in claim 1 and further including a plurality of additional posts releasably fixed to selected ones of said plurality of rails.

3. The system defined in claim 1 and further including means for releasably fixing each rail to the tray bottom wall through the holes underlying that rail.

4. The system defined in claim 1 wherein
   each rail defines a keyway having an internal wall;
   said post one end defines a key configured to slide in said keyway, and
   said fixing means include means for pressing the key against said keyway wall.

5. The system defined in claim 1 wherein
   each rail defines a key;
   said post one end defines a keyway configured to slide along said rail, and
   said fixing means include means on the post for engaging the rail.

6. A retention device for fixating medical instruments in a sterilization tray of the type having a bottom wall with a rectangular array of ventilation holes, said device comprising
   an elongated generally rectangular rail having opposite walls;
   a plurality of projections extending from one of said walls and spaced apart along said rail a distance equal to, or an integral multiple of, the hole spacing, said projections being sized to plug into the holes;
   a plurality of posts, each post having opposite ends;

means for keying one end of each post to the other wall of said rail so that the post can slide along the rail to a selected position, and fixing means on each post for releasably fixing the position of the post on the rail, said fixing means including a threaded fastener threaded axially through said post, said fastener having an end portion engaging said rail so that when the post and fastener are rotated relatively in one direction, the post is clamped to the rail and when the post and fastener are rotated relatively in the opposite direction the post is unclamped from the rail.

7. The device defined in claim 6 and further including securing means attached to the posts for releasably securing the rail to a tray bottom wall through the holes therein.

\* \* \* \* \*